(12) United States Patent
Naybour

(10) Patent No.: US 6,200,349 B1
(45) Date of Patent: Mar. 13, 2001

(54) PROSTHETIC COMPONENT

(75) Inventor: John Naybour, Mold (GB)

(73) Assignee: Johnson & Johnson Professional, Inc., Raynham, MA (US)

( * ) Notice: Subject to any disclaimer, the term of this patent is extended or adjusted under 35 U.S.C. 154(b) by 0 days.

(21) Appl. No.: 09/345,142

(22) Filed: Jun. 30, 1999

(30) Foreign Application Priority Data

Jul. 1, 1998 (GB) .................................................. 9814274

(51) Int. Cl.$^7$ ........................................................ A61F 2/36
(52) U.S. Cl. ............................................................ 623/23.15
(58) Field of Search ............................. 623/20.36, 22.4, 623/22.41, 22.42, 22.45, 23.15, 23.18, 23.23, 23.24, 23.25, 23.26, 23.27, 23.29, 23.31, 23.32, 23.33, 23.34, 23.35

(56) References Cited

FOREIGN PATENT DOCUMENTS

| 3902775 | * | 8/1990 | (DE) | ........................................ | 623/23 |
| 0243298 | * | 10/1987 | (EP) | ........................................ | 623/23 |
| 2549717 | * | 2/1985 | (FR) | ........................................ | 623/23 |

\* cited by examiner

*Primary Examiner*—David J. Isabella

(57) ABSTRACT

A prosthetic component which can be in the form of a hip stem (1) is provided with a proximal portion (2) and a distal portion (4) terminating at a distal end (5). The distal portion (4) has at least two slots (6) disposed longitudinally in the distal portion (4). The distal portion (4) of the hip stem (1) has a hollow centre (8). The hip stem (1) can be compressed to expand the diameter of the distal portion (4) by buckling the legs (13) between the slots (6) in the form of a stent or Chinese lantern.

14 Claims, 6 Drawing Sheets

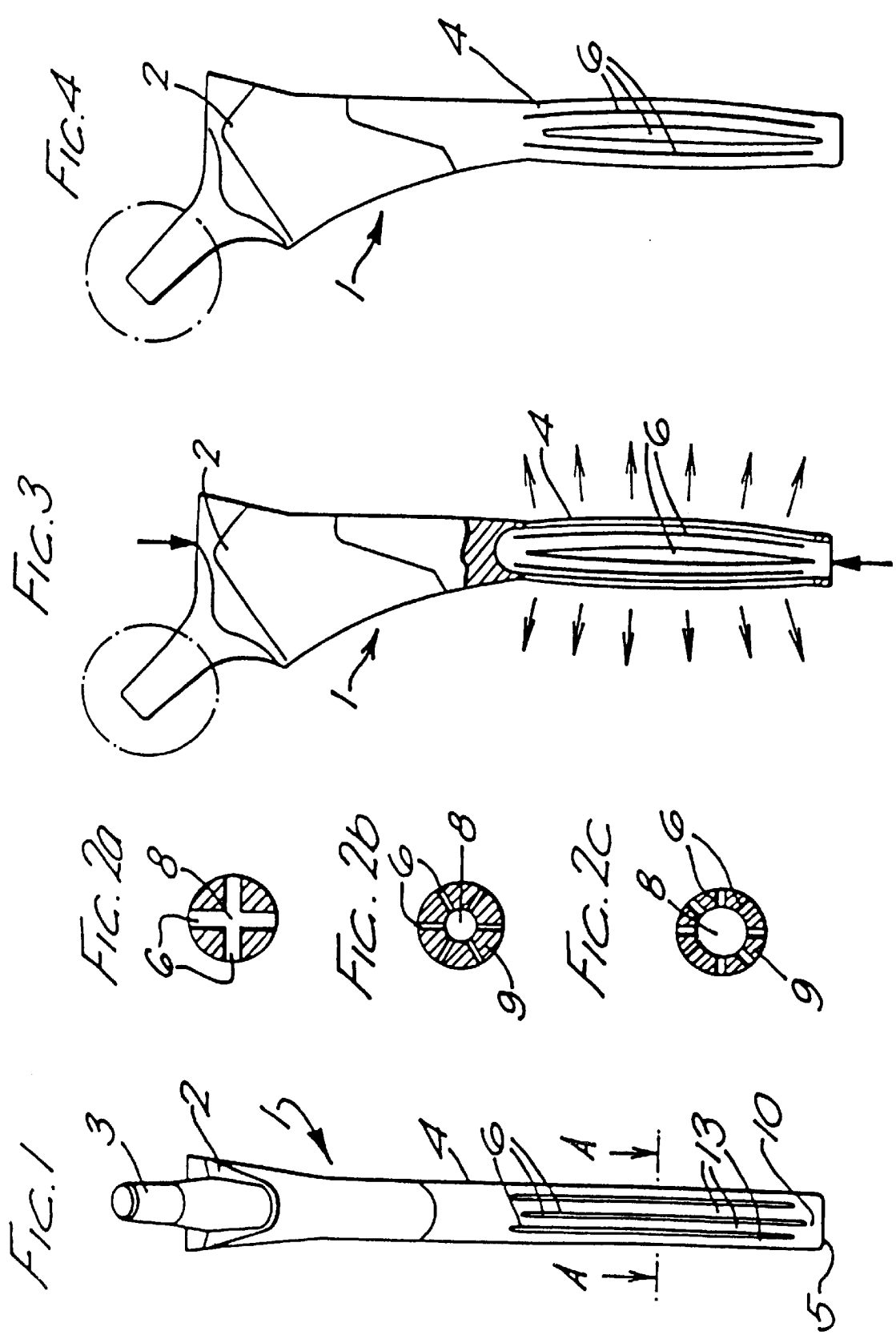

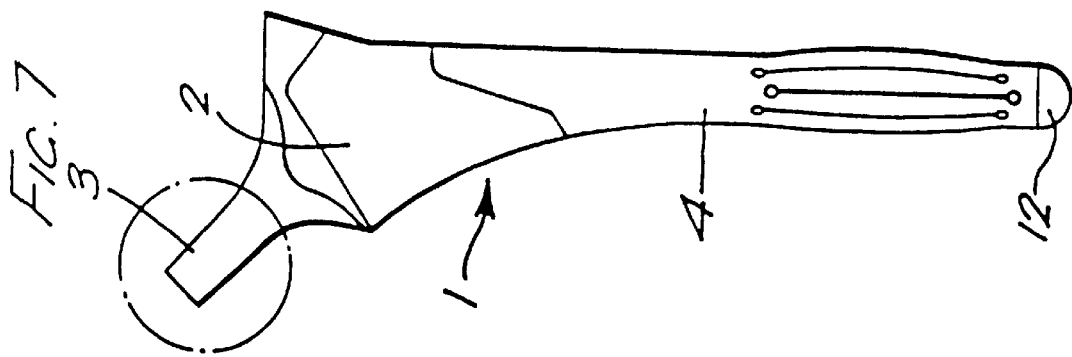
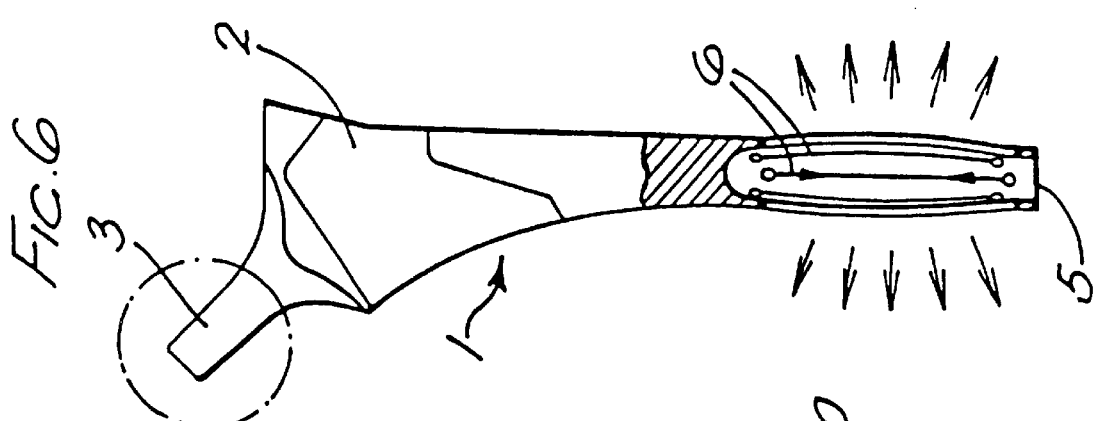
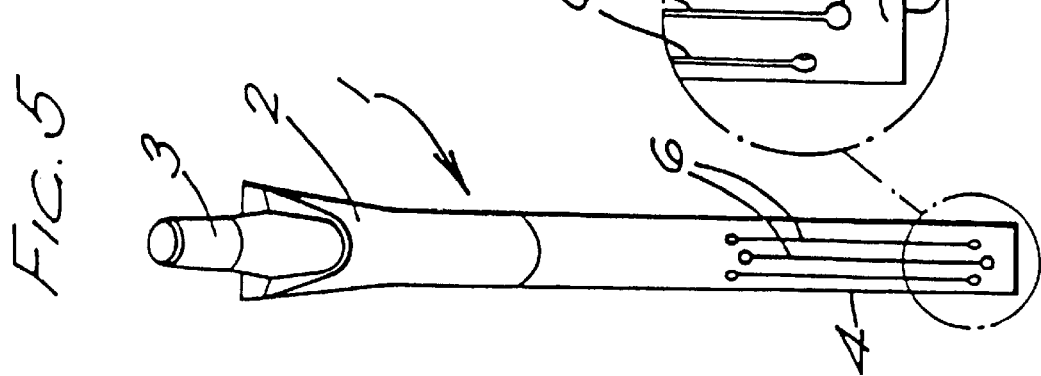

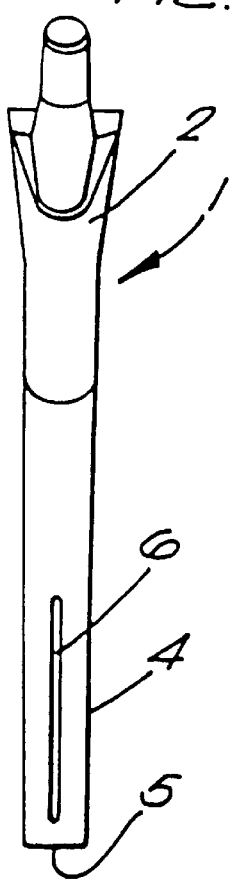
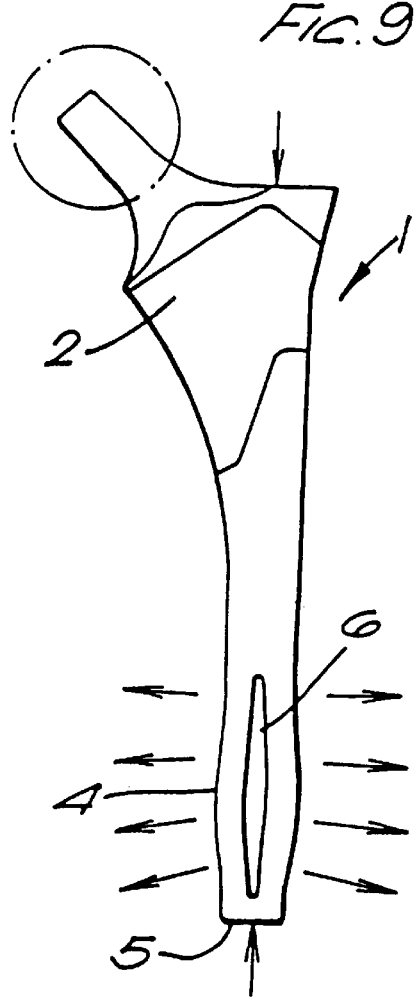
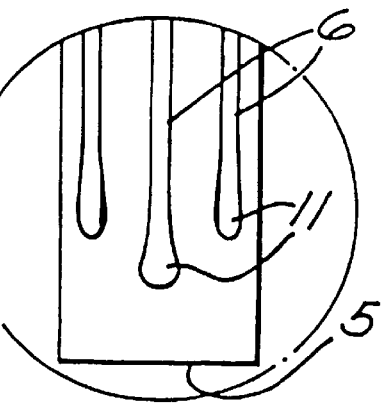
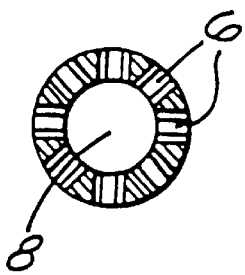

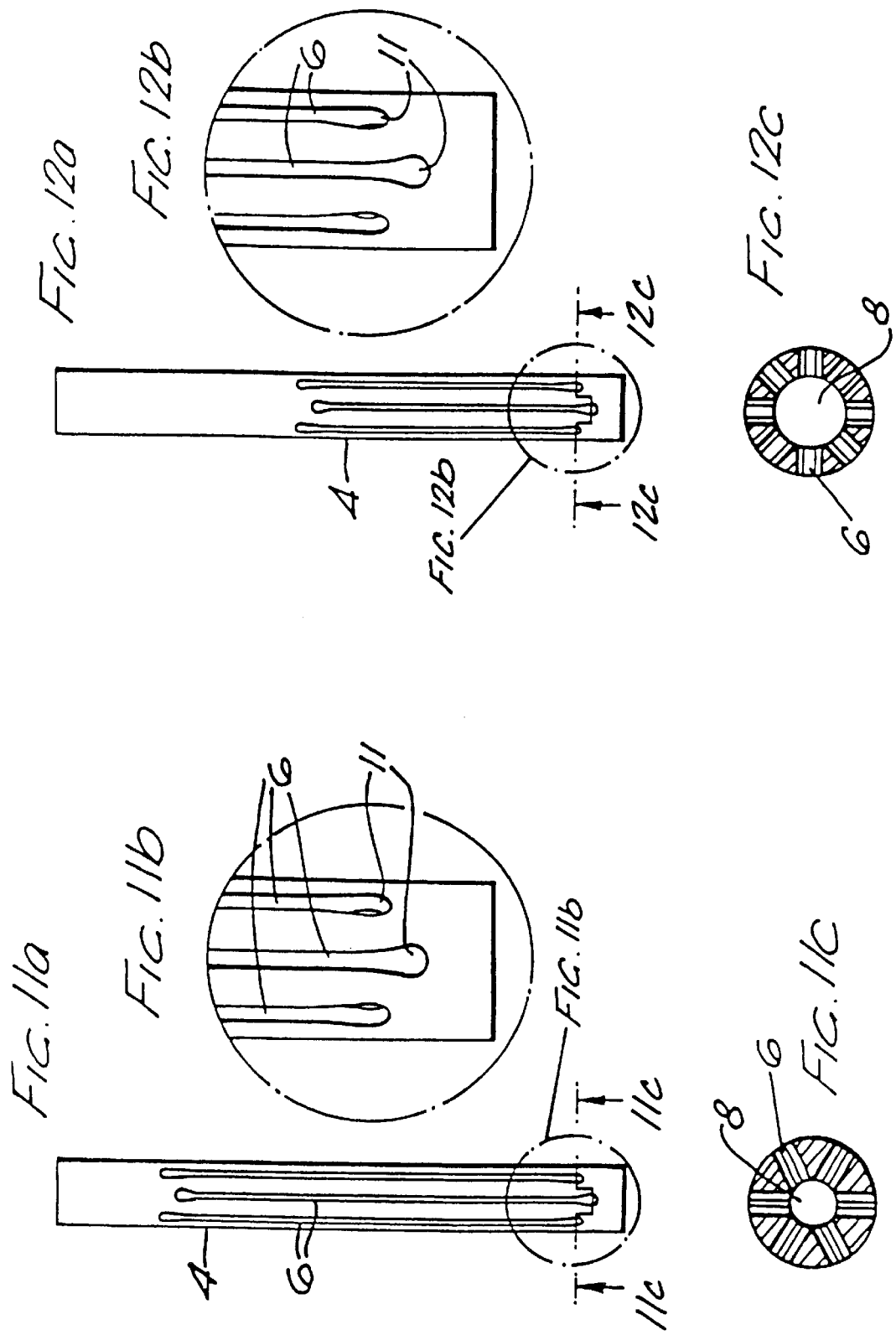

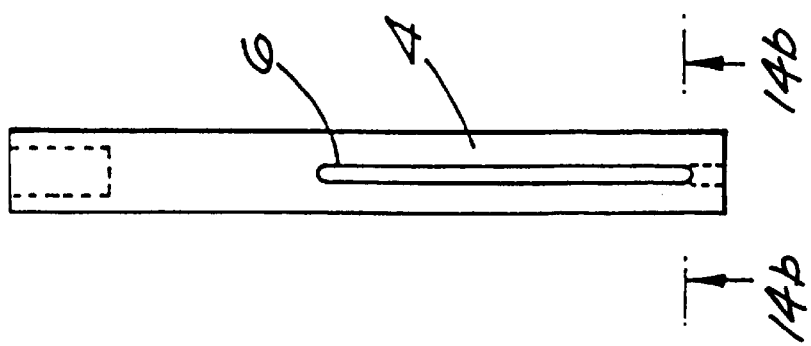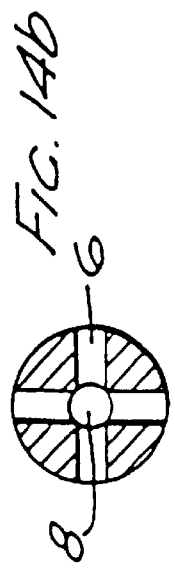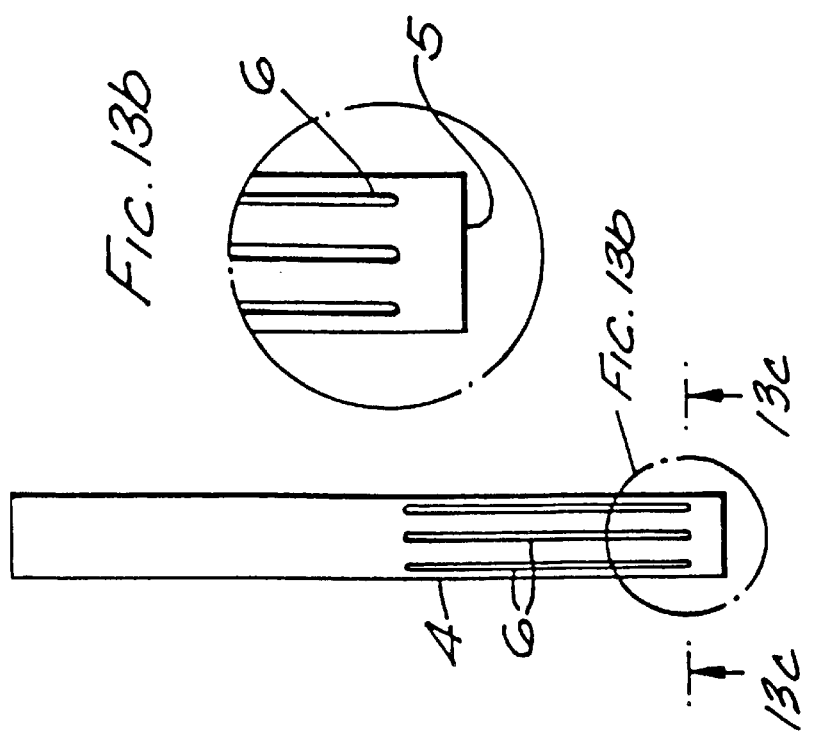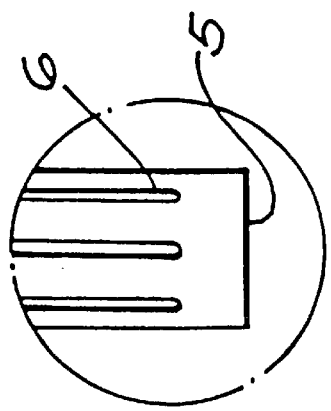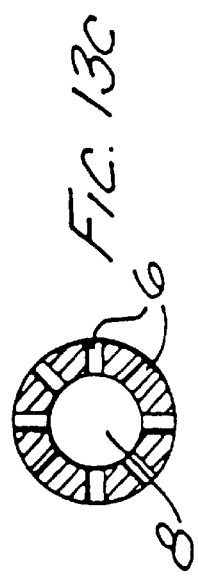

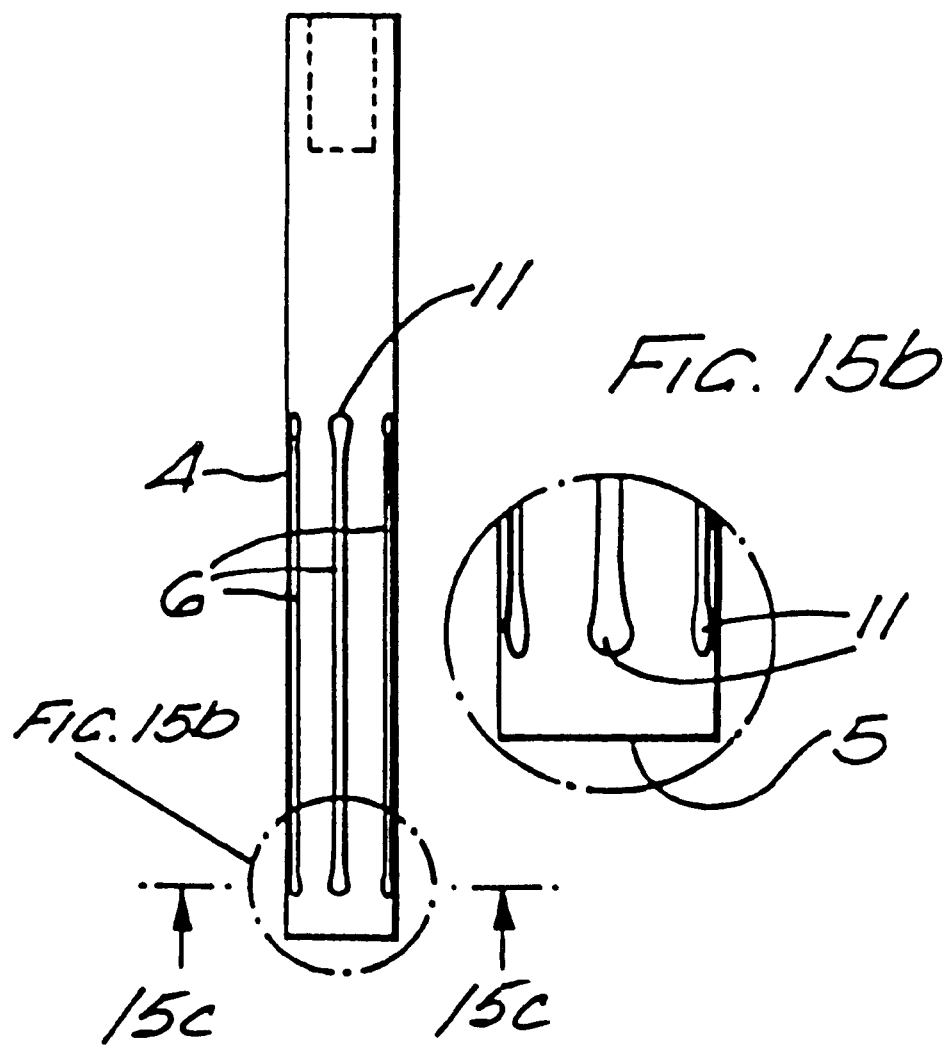
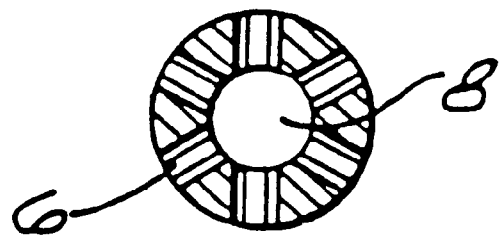

PROSTHETIC COMPONENT

This invention relates to a prosthetic component for insertion in a bone cavity of a patient. In particular the invention is described in the form of a prosthetic hip stem for insertion in a femur, although the prosthetic component of the invention could be for a shoulder, knee or other application.

In the case of prosthetic hip stems, cementless prosthetic hip stems are known in which a prosthetic hip stem is inserted in a patient's femur without surrounding bone cement. The distal portion of the hip stem gives initial stability within the bone cavity. In the long term, bone growth holds the proximal portion of the hip stem in place. In order to suit different patients, five different sizes of proximal portions of the hip stem are usually available to the surgeon. In addition, four different sizes of distal portions of the hip stem are also available. This results in a range of 20 differently shaped and sized hip stems from which the surgeon can choose the correct size for a particular patient.

If the distal diameter of the hip stem can be modified during an operation, this removes the need for hip stems with different distal portions to be available to the surgeon. The number of hip stems could be reduced to five for the five different proximal portions.

A known form of hip stem with an expandable distal portion has a distal portion with at least two slots extending from the distal end of the hip stem. Mandrels are forced into the slots to bend the distal portion of the hip stem outwardly thereby expanding the diameter of the distal portion of the hip stem.

A disadvantage of distal slots of this nature is that they limit the length of the leg due to stress at the end of the slots where bending occurs. Up to 2.5 mm expansion to the diameter of the distal portion of the hip stem has been found to be possible. Hip stems of this type also have the disadvantage that each leg defined by the slots must be strong enough to take the force of the patient's weight to avoid breaking.

According to the present invention there is provided a prosthetic component for insertion in a patient's bone, the prosthetic component comprising a first portion and a second portion having an end, wherein the second portion is hollow with at least two longitudinal slots formed therein, and wherein the slots are closed at the end of the second portion of the component.

Preferably, the first and second portions are proximal and distal portions respectively wherein, in use, the distal portion has a distal end which is inserted further into the patient's bone.

The prosthetic hip stem may be a hip stem and the patient's bone is a femur. Preferably, the prosthetic hip stem is a cementless hip stem.

Preferably, there are provided at least four slots in the second portion of the component. The slots may be staggered such that alternate slots are displaced longitudinally in the component. Alternatively, the slots may be level in the longitudinal direction of the component.

Preferably, the slots are equally disposed circumferentially around the component.

The length of the slots in a component in the form of a hip stem may be in the range of 35 to 65 mm or larger. The slot width may be 0.5–2 mm or wider. Preferably, the distal portion of the hip stem can expand to a diameter of 21 mm and larger.

The slots may end in terminating holes. The holes may have a tear-drop shape.

Preferably, the end of the second portion of the component is closed. Preferably, the component is formed of titanium alloy or a similar material. Preferably, the second portion of the component is plastically deformable such that it holds its deformed position.

The prosthetic component may be a shoulder or knee component.

According to a second aspect of the present invention, there is provided a method of manufacture of a prosthetic component for insertion in a patient's bone comprising providing a component with a first portion and a second portion ending in an end; cutting slots in a second portion of the component; removing cut material from inside the second portion of the component.

Preferably, the first and second portions are proximal and distal portions respectively wherein, in use, the distal portion has a distal end which is inserted further into the patient's bone.

The prosthetic component may be a hip stem. Alternatively, the prosthetic component may be for use in a shoulder or knee application.

Preferably, the method includes the step of applying pressure externally to the distal end of the component to compress the distal portion of the component.

Preferably, the slots are machined through a side of the distal portion of the component. Preferably, at least two slots are formed in the distal portion of the component. Most preferably, at least four slots are formed.

Embodiments of prosthetic components in the form of hip stems in accordance with the present invention are now described, by means of example only, with reference to the accompanying drawings in which:

FIG. 1 is a front elevation of a first embodiment of a prosthetic hip stem in accordance with the present invention before use;

FIGS. 2a, 2b and 2c are alternative sections through line A—A of FIG. 1 with different sizes and numbers of slots;

FIG. 3 is a side elevation of the hip stem of FIG. 1 in which pressure has been applied externally to expand the stem;

FIG. 4 is a side elevation of the hip stem of FIG. 3 expanded to the required size;

FIG. 5 is a front elevation of a second embodiment of a prosthetic hip stem in accordance with the present invention;

FIG. 6 is a side elevation of the prosthetic hip stem of FIG. 5 with pressure applied internally to expand the stem;

FIG. 7 is a side elevation of the hip stem of FIG. 6 expanded to the required size with the distal end plugged;

FIG. 8 is a third embodiment of a prosthetic hip stem in accordance with the present invention with a short slot;

FIG. 9 is a side elevation of the prosthetic hip stem of FIG. 8 showing pressure applied externally to expand the stem;

FIG. 10a, FIG. 10b and FIG. 10c are a side elevation, a detail and a cross-section of a distal portion of a prosthetic hip stem in accordance with the present invention showing an arrangement of slots;

FIG. 11a, FIG. 11b and FIG. 11c are a side elevation, a detail and a cross-section of an alternative arrangement of slots in a distal portion of a prosthetic hip stem in accordance with the present invention;

FIG. 12a, FIG. 12b and FIG. 12c are a side elevation, a detail and a cross-section of a further arrangement of slots in a distal portion of a prosthetic hip stem in accordance with the present invention;

FIG. 13a, FIG. 13b and FIG. 13c are a side elevation, a detail and a cross-section of a further arrangement of slots in a distal portion of a prosthetic hip stem in accordance with the present invention;

FIG. 14a and FIG. 14b are a side elevation and cross-section of a further arrangement of slots in a distal portion of a prosthetic hip stem in accordance with the present invention; and FIGS. 15a, 15b and 15c are a side elevation, a detail and a cross-section of a further arrangement of slots in a distal portion of a prosthetic hip stem in accordance with the present invention.

Referring to the drawings, the first embodiment of a prosthetic hip stem 1 is shown in FIGS. 1 to 4. The prosthetic hip stem 1 has a proximal portion 2 with a neck 3 for attachment to a condylar portion. The hip stem 1 has a distal portion 4 which is generally cylindrical terminating at a distal end 5. The distal portion 4 of the hip stem 1 has a hollow centre 8 surrounded by a wall 9.

A plurality of slots 6 are formed in the distal portion 4 of the hip stem 1. The slots 6 extend longitudinally along the distal portion 4 of the hip stem 1. The slots 6 are equally spaced circumferentially around the cylindrical shape of the distal portion 4. Alternate slots may be staggered longitudinally. The slots 6 extend through the wall 9 of the distal portion 4 to the hollow centre 8 of the distal portion 4. The shape of the slots 6 may define the hollow centre 8 of the distal portion 4. The slots 6 define legs 13 between the slots 6.

FIGS. 2a, 2b and 2c show alternative sections of the hip stem 1 shown in FIG. 1. The alternative sections show 4, 6 and 8 slot arrangements with differing depths and widths of slots 6. FIG. 2a shows four slots, 3.6 mm deep and 2 mm wide. FIG. 2b shows 6 slots, 3 mm deep and 0.5 mm wide. FIG. 2c shows 8 slots, 2 mm deep and 1 mm wide.

The hip stem 1 is expanded by applying pressure along the longitudinal length of the hip stem 1 as shown in FIG. 3. The hollow distal portion 4 of the hip stem 1 expands in diameter as the slots 6 expand.

The distal end 5 is in the form of a closed ring 10 such that the slots 6 do not extend to the distal end 5 of the hip stem 1 enabling the legs 13 defined by the slots 6 to buckle outwardly.

A second embodiment of the present invention is shown in FIGS. 5 to 7 in which elongated slots are provided having terminating holes 11 at the ends of the slots 6. The slots 6 may terminate in holes 11 of tear-drop shapes as shown in FIGS. 10a to 10c, 11a to 11c, 12a to 12c and 15a to 15c.

Pressure can be applied internally to expand the hip stem 1 as shown in FIG. 6. A cap 12 can be applied to the distal end 5 of the hip stem 1 to seal the distal end 5 as shown in FIG. 7 to prevent the ingress of material during insertion of the hip stem 1 in the femur.

A third embodiment of the present invention is shown in FIGS. 8 and 9 in which four slots 6 of short length are provided. Reduction in slot length moves the point of maximum expansion distally along the hip stem 1.

Alternative arrangements of straight slots are shown in FIGS. 13a to 13c and 14a to 14c. The slot length can range from approximately 35 to 65 mm.

The hip stem 1 can be manufactured by machining the slots 6 through the wall 9 of the distal portion 4 of the hip stem 1. The hip stem 1 can be drilled to hollow out the hollow centre 8 of the distal portion 4 of the hip stem 1 before the slots 6 are formed. Alternatively, machining the slots 6 can remove the centre portion of the distal portion 4 making it hollow.

The aim of the present invention is to provide a low cost cementless hip replacement system with a distal portion 4 which is expandable. The function of the distal portion 4 of a hip stem 1 is to fill the canal of the bone and thus give greater stability to the hip stem 1. Five sizes of proximal portions 2 of the hip stem 1 cover almost all anatomical situations. However, the distal portion 4 of a hip stem 1 requires a greater size range and an expandable distal portion 4 of a hip stem 1 achieves this range.

It is desirable to be able to modify the size of the distal portion 4 of a hip stem 1 with final sizing of the distal portion 4 of the hip stem 1 taking place in the operating theatre at the time of operation.

It has been found that providing a stent-like or Chinese lantern arrangement in which slots 6 are provided in the distal portion 4 of the hip stem 1 with a closed distal end 5 such that the legs 13 defined by the slots 6 bow outwardly when the hip stem 1 is compressed, results in compressive loading and greater bending. A gentle curvature of the legs 13 along the length of the slots 6 can result in an expansion of a diameter of the distal portion 4 of ideally 9 to 21 mm. The legs 13 are deformed plastically when compressed such that they maintain their expanded position.

The slots 6 must have sufficient width to avoid fretting contact between adjacent legs 13 and must have sufficient width to discourage bone growth. For example, a width of 1 mm to 2 mm is considered to be suitable.

The radial thickness of the wall 9 of the distal portion 4 must be chosen to ensure outwards buckling of the legs 13 when compressive expanded as opposed to sideways buckling. A suitable radial wall thickness also avoids difficult machining of a small central hole of the distal portion 4.

The following table shows experimental expansion results of hip stems 1 with 4, 6 and 8 slot options:

- 8 slot data
  compression force 1 tonne (calculated value)
  stem deflection: 1.2 mm at mid column    2.1 mm at distal tip
                                           @70N load
- 6 slot data
  compression force 3.5 tonne
  stem deflection: 0.5 mm at mid column    0.8 mm at distal tip
                                           @70N load
- 4 slot data
  compression force 2.6 tonne
  stem deflection: 0.4 mm at mid column    0.7 mm at distal tip
                                           @70N load
- For comparison, 10 mm titanium bar has
  stem deflection: 0.08 mm at mid column   0.3 mm at distal tip
                                           @70N load Maximum expansion occurs midway along the column length.

The prototype 6-slot stem survived expansion from 10 mm to 21 mm without damage.

A short length of slot 6 as shown in FIGS. 8 and 9 has the effect of moving the point of maximum expansion towards the distal end 5 of the hip stem 1. An increased compression load is required for expansion. The following table shows the expansion figures for the short slot embodiment:

8 slot data
   compression force 2 tonnes (calculated value)
   stem deflection: 0.89 mm at distal tip @70N load
6 slot data
   compression force 7 tonnes
   stem deflection: 0.64 mm at distal tip @70N load
4 slot data
   compression force 5.2 tonnes
   stem deflection: 0.52 mm at distal tip @70N load The distal portions 4 of the hip stem 1 are formed of titanium 6/4 alloy in an annealed condition.

The prosthetic component and method of manufacture have been described by means of an example of a hip stem. The prosthetic component of the present invention can be used in shoulder, knee and other applications with the expandable portion being at any desired portion of the component.

Modifications and improvements can be made to the foregoing without departing from the scope of the present invention.

What is claimed is:

1. A prosthetic component for insertion in a patient's bone, the prosthetic component comprising a proximal portion and a distal portion, the distal portion ending at an end, wherein the distal portion is hollow with at least two longitudinal slots formed therein, and wherein the slots have a proximal end and a distal end and are closed at each end the distal end of the slots terminated at a position on the stem spaced proximally from the distal end of the prosthetic component, the diameter of the distal portion capable of expanding under pressure applied axially to the prosthesis in a direction from the proximal portion to the distal portion.

2. A prosthetic component as claimed in claim 1 wherein the prosthetic component is a hip stem and the patient's bone is a femur.

3. A prosthetic component as claimed in claim 1, wherein there are provided at least four slots in the distal portion of the component.

4. A prosthetic component as claimed in claim 1, wherein the slots are staggered such that the ends of alternate slots are displaced longitudinally in the component.

5. A prosthetic component as claimed in claim 1 wherein the ends of the slots are at the same position in the longitudinal direction of the component.

6. A prosthetic component as claimed in claim 1, wherein the slots are equally disposed circumferentially around the component.

7. A prosthetic component as claimed in claim 2, wherein the length of the slots in the hip stem is in the range of 35 to 65 mm.

8. A prosthetic component as claimed in claim 2, wherein the slot width in the hip stem is 0.5–2 mm.

9. A prosthetic component as claimed in claim 2, wherein the distal portion of the hip stem can expand to a diameter of 21 mm.

10. A prosthetic component as claimed in claim 1, wherein the slots end in terminating holes.

11. A prosthetic component as claimed in claim 10, wherein the holes have a tear-drop shape.

12. A prosthetic component as claimed claim 1, wherein the end of the second portion of the component is closed.

13. A prosthetic component as claimed in claim 1, wherein the component is formed of a metal selected from the group consisting of titanium alloy and stainless steel.

14. A prosthetic component as claimed claim 1, wherein the prosthetic component is a shoulder or knee component.

\* \* \* \* \*